United States Patent
Deutinger et al.

(10) Patent No.: US 10,714,228 B2
(45) Date of Patent: Jul. 14, 2020

(54) METHOD FOR PRODUCING A MICROSTRUCTURE COMPONENT, MICROSTRUCTURE COMPONENT AND X-RAY DEVICE

(71) Applicant: Siemens Healthcare GmbH, Erlangen (DE)

(72) Inventors: Andrea Deutinger, Forstern (DE); Joerg Zapf, Munich (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 0 days.

(21) Appl. No.: 16/281,299

(22) Filed: Feb. 21, 2019

(65) Prior Publication Data
US 2019/0267149 A1 Aug. 29, 2019

(30) Foreign Application Priority Data
Feb. 28, 2018 (EP) .................... 18159259

(51) Int. Cl.
*G21K 1/00* (2006.01)
*G21K 1/06* (2006.01)
(Continued)

(52) U.S. Cl.
CPC ............... *G21K 1/06* (2013.01); *A61B 6/484* (2013.01); *B81C 1/00539* (2013.01);
(Continued)

(58) Field of Classification Search
CPC .... G01K 1/06; G21K 1/025; G21K 2207/005; G21K 2201/06; B81C 1/00539;
(Continued)

(56) References Cited

U.S. PATENT DOCUMENTS 8,223,924 B2    7/2012  Borner et al.
9,348,067 B2 *  5/2016  Vogtmeier ........... G02B 5/1857
(Continued)

FOREIGN PATENT DOCUMENTS

CN      101813796 B    7/2012
DE   102010017425 A1   12/2011
(Continued)

OTHER PUBLICATIONS

Astrova E V et al: "Structure and composition of silicon microarrays subjected to cyclic insertion and extraction of lithium"; Technical Physics; Pleiades Publishing /AIP; Melville; NY; US; Bd. 60; Nr. 4; pp. 531-540; XP035492289; ISSN: 1063-7842: DOI: 10.1134/SI063784215040040;.
(Continued)

*Primary Examiner* — Kiho Kim
(74) *Attorney, Agent, or Firm* — Harness, Dickey & Pierce, P.L.C.

(57) ABSTRACT

A method for producing a microstructure component, a microstructure component and an x-ray device are disclosed. In the method, a plurality of punctiform injection structures are inserted in a grid in a first substrate direction and a second substrate direction, standing at right angles thereto, into a first surface of a wafer-like silicon substrate. The injection structures are lengthened into drilled holes in the depth direction of the silicon substrate in a first etching step. A second surface of the silicon substrate is then at least partly removed for rear-side opening of the drilled holes in a second etching step and in a third etching step, an etching medium acting anisotropically is poured alternately through the drilled holes from both surfaces of the silicon substrate, so that drilled holes arranged next to one another in the first substrate direction connect to form a column running in the first substrate direction.

22 Claims, 4 Drawing Sheets

(51) Int. Cl.
*B81C 1/00* (2006.01)
*G21K 1/02* (2006.01)
*G02B 5/18* (2006.01)
*A61B 6/00* (2006.01)

(52) U.S. Cl.
CPC ......... *G02B 5/1842* (2013.01); *G02B 5/1857* (2013.01); *G02B 5/1871* (2013.01); *G21K 1/025* (2013.01); *G21K 2201/06* (2013.01); *G21K 2207/005* (2013.01)

(58) Field of Classification Search
CPC .. G02B 5/1857; G02B 5/1842; G02B 5/1871; A61B 6/4291; A61B 6/484
See application file for complete search history.

(56) References Cited

U.S. PATENT DOCUMENTS

| | | | |
|---|---|---|---|
| 9,763,634 B2 * | 9/2017 | Preusche | A61B 6/4035 |
| 2012/0219916 A1 | 8/2012 | Teshima et al. | |
| 2012/0263274 A1 | 10/2012 | Ouchi | |
| 2013/0148780 A1 | 6/2013 | Mohr et al. | |
| 2013/0181130 A1 | 7/2013 | Itoh et al. | |

FOREIGN PATENT DOCUMENTS

| | | |
|---|---|---|
| DE | 102010061481 A1 | 6/2012 |
| DE | 102015201741 A1 | 8/2016 |
| JP | 3599325 B2 | 12/2004 |
| JP | 3627856 B2 | 3/2005 |
| JP | 2012132793 A | 7/2012 |
| WO | WO 2017036729 A1 | 3/2017 |

OTHER PUBLICATIONS

Chernienko A. V. et al: "Zigzag structures obtained by anisotropic etching of macroporous silicon"; Technical Physics Letters: Bd. 39 Nr. 11; pp. 990-993; XP55502266; US; ISSN: 1063-7850; DOI: 10.1134/SI063785013110175;.

European Search Report for European Patent Application No. 18159259 dated Aug. 27, 2018.

* cited by examiner

METHOD FOR PRODUCING A MICROSTRUCTURE COMPONENT, MICROSTRUCTURE COMPONENT AND X-RAY DEVICE

PRIORITY STATEMENT

The present application hereby claims priority under 35 U.S.C. § 119 to European patent application number EP 18159259.3 filed Feb. 28, 2018, the entire contents of which are hereby incorporated herein by reference.

FIELD

Embodiments of the invention generally relate to a method for producing a microstructure component, in particular an x-ray phase contrast grating; to a microstructure component, in particular to an x-ray phase contrast grating; and also to an x-ray device with such a grating.

BACKGROUND

In the area of x-ray imaging, in particular in the medical area, what is referred to as the Talbot effect is used in some cases. This enables more precise image information to be generated, in that the contrast of the images created is improved by incorporating a phase shift of the x-rays caused by an examination object. In such cases a so-called (x-ray) phase contrast grating is regularly used, with is introduced into the beam path. Such a grating is usually formed in this case by lamellae aligned in the direction of the x-ray radiation and made from an x-ray absorbing material. Usually the wall thickness and the distances of these lamellae from one another lie in the one to low two-digit millimeter range. Also the thickness (or: height) of the grating as a whole in the irradiated area usually lies at a maximum of one millimeter. Thus such a contrast phase grating involves a microstructure component.

Because of the small dimensions, these phase contrast gratings are mostly produced by etching methods in silicon wafers and subsequent filling of the etched recesses with x-ray absorbing material for embodying the lamellae. This is known for example from DE 10 2015 201 741 A1.

SUMMARY

The inventors have recognized that, frequently, the problem in such a case is that the phase contrast grating should ideally be tailored to the local radiation direction of the radial rays emanating from a mostly punctiform radiation source. I.e. the lamellae should ideally be placed at an angle to one another.

At least one embodiment of the present invention is directed to an improved microstructure component.

At least one embodiment, in accordance with the invention, is directed to a method for producing such a microstructure component. Furthermore, at least one embodiment, in accordance with the invention, is directed to a microstructure component. Moreover, at least one embodiment, in accordance with the invention, is directed to an x-ray device. Forms of embodiment and developments of the invention that are advantageous and in some cases inventive per se are set out in the dependent claims and in the description given below.

The inventive method of at least one embodiment serves to produce a microstructure component. In accordance with at least one embodiment of the method, a plurality of punctiform injection structures, especially separated from one another, are inserted in a grid, which is predetermined in a first substrate direction and in a second substrate direction—lying at right angles to the first—into a first surface of a wafer-like silicon substrate, in particular into a wafer or a part of a wafer. Following on from this the injection structures are lengthened into drilled holes in (preferably only) the depth direction (or also: thickness direction) of the silicon substrate in a first etching step—i.e. deepened. Subsequently a second surface opposite to the first surface of the silicon substrate is at least partly removed in a second etching step for rear-side opening of the drilled holes. Then, in a third etching step, an anisotropically effective etching medium—in particular an etching solution—is poured alternately from both surfaces of the silicon substrate through the drilled holes. The etching medium in this case is poured alternately through the drilled holes until such time as the drilled holes arranged next to one another in the first substrate direction connect to each other in a column running in the first substrate direction.

The inventive method of at least one embodiment, for producing a microstructure component, comprises:

inserting a plurality of punctiform injection structures in a grid in a first substrate direction and inserting a second substrate direction, standing at right angles to the first substrate direction, into a first surface of a wafer-like silicon substrate;

lengthening, in a first etching step, the punctiform injection structures into drilled holes in a depth direction of the silicon substrate;

at least partly removing, in a second etching step, a second surface of the silicon substrate, lying opposite the first surface, for rear-side opening of the drilled holes; and pouring in a third etching step, an etching medium, effective anisotropically, alternately through the drilled holes from both surfaces of the silicon substrate, so that drilled holes arranged next to one another in the first substrate direction connect to form a column running in the first substrate direction.

The inventive microstructure component of an embodiment, in particular the phase contrast grating formed by this component, is produced in accordance with the method of at least one embodiment described. Preferably the microstructure component is also bent in the case of the phase contrast grating. In particular, at least one embodiment the inventive microstructure component has the same features and advantages as those produced by the method of production of at least one embodiment described.

The inventive x-ray device of at least one embodiment, has the phase contrast grating formed by the microstructure component described above. Thus, the inventive x-ray device of at least one embodiment also shares the features and advantages described above. In particular, when the x-ray device is used as per specifications, the columns of the microstructure component described above are filled with the material that absorbs x-rays to form the grating lamellae.

BRIEF DESCRIPTION OF THE DRAWINGS

Example embodiments of the invention will be described below, in greater detail with reference to a drawing. In the figures.

Parts corresponding to one another are always labeled with the same reference characters in all figures

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

The inventive method of at least one embodiment serves to produce a microstructure component. In accordance with at least one embodiment of the method, a plurality of punctiform injection structures, especially separated from one another, are inserted in a grid, which is predetermined in a first substrate direction and in a second substrate direction—lying at right angles to the first—into a first surface of a wafer-like silicon substrate, in particular into a wafer or a part of a wafer. Following on from this the injection structures are lengthened into drilled holes in (preferably only) the depth direction (or also: thickness direction) of the silicon substrate in a first etching step—i.e. deepened. Subsequently a second surface opposite to the first surface of the silicon substrate is at least partly removed in a second etching step for rear-side opening of the drilled holes. Then, in a third etching step, an anisotropically effective etching medium—in particular an etching solution—is poured alternately from both surfaces of the silicon substrate through the drilled holes. The etching medium in this case is poured alternately through the drilled holes until such time as the drilled holes arranged next to one another in the first substrate direction connect to each other in a column running in the first substrate direction.

Preferably in particular an (x-ray) phase contrast grid is produced as the microstructure component by the method described above.

Further preferably directions are employed as the first and second substrate direction, in which crystal planes referred to as "(111) crystal planes" of the silicon substrate pass through a "(100) crystal plane" of the silicon substrate aligned in parallel to the first surface.

The fact that in the first etching step the injection structures are deepened in the depth direction—preferably with small or negligible widening—to the drilled holes, advantageously enables these to be molded out with a comparatively higher diameter to depth ratio (also; "aspect ratio"). Since in the third etching step a number of drilled holes arranged next to one another are connected to form the column, the substrate material merely needs to be removed between two adjacent drilled holes in the first substrate direction, whereby it is also advantageously made possible to keep the aspect ratio (i.e. the width-to-height ratio) of the column formed from the drilled holes as high as possible— thus preferably to only allow a comparatively small "widening" in the second substrate direction. Preferably for this purpose a number of injection structures and thus also a number of drilled holes are distributed over the longitudinal extent of each of the columns as per specifications. A high aspect ratio in this case is regularly advantageous for especially precise embodiment properties when the microstructure component is used in an x-ray device as the (x-ray) phase contrast grating.

In a preferred variant embodiment of the method the injection structures are arranged in the second substrate direction at a first distance from one another. In the first substrate direction they are combined into groups in each case. These groups each comprise a subordinate number of the injection structures. Moreover the injection structures within these groups are arranged in relation to one another at a second distance reduced by a factor of 0.2-0.6, preferably of 0.3-0.5 compared to the first distance. I.e. the injection structures, within the groups and thus in the first substrate direction, are at a distance from one another that is at least 40 percent smaller compared to the first distance. This makes it possible in a simple manner, for—as described above—the column in the third etching step to be embodied in the first substrate direction by connecting the individual drilled holes in a comparatively short time and to be separated from one another in each case in the second substrate direction by a web (referred to below as a "longitudinal web") (as well as, by comparison with the longitudinal extent of the column, advantageously to only undergo a slight widening out).

In an advantageous development, the groups previously described are arranged following on from one another in the first substrate direction at a third distance that is greater by comparison with the second distance. I.e. the groups are separated from one another in the first spatial direction (in particular further as the injection structures within the groups). The third distance is selected in this case such that, in the third etching step, the edge-side injection structures of each of the groups do not coalesce with the injection structures of the adjacent group lying in the first substrate direction. In particular this advantageously makes it possible, in the third etching step, seen in the first substrate direction to embody a number of consecutive columns, which are separated from one another in each case by a transverse web, which is aligned in the direction of the second substrate direction. Through this the mechanical stability (in particular a flexural strength) of the silicon substrate penetrated by the columns, seen in the second substrate direction, is advantageously increased.

In an expedient variant embodiment of the method, the groups described above, which follow one another, seen in the second substrate direction, are arranged offset to one another in relation to their longitudinal extent along the first substrate direction, in particular alternating with one another. I.e. each of the groups and thus each of the columns formed therefrom is arranged shifted in the first substrate direction by comparison with the adjacent group or the adjacent column in the second substrate direction. In this case—in particular in the case of the transverse webs described above—the transverse webs embodied in the third etching step "meander", seen in the second substrate direction, about the columns running the first substrate direction (i.e. the transverse webs, seen in the second substrate direction, do not lie flush with one another or at least do not all lie flush with one another). The advantageous result of this is that the mechanical stability of the microstructure component formed is increased in relation to a bending about a bending axis running in the first substrate direction and in particular compared to columns that run continuously in the first substrate direction, but that a flexibility sufficient for a bending about this bending axis is still made possible. The latter is advantageous in order—in particular in the case of the phase contrast grating—to make possible an adaptation of the grating lamellae preferably embodied in the columns to the local direction of radiation, in particular for being able to bend the phase contrast grating in a simple way about this bending axis (preferably along a circular cylindrical surface).

In a development expedient for production technology the groups described above are arranged offset in relation to one another by about (preferably exactly) half of their longitudinal extent in the first substrate direction. Thus groups lying in the "column rows" running in the first substrate direction, for each row increment (i.e. in each adjacent column row in the second substrate direction) are shifted by around half in the longitudinal direction. This preferably makes possible a symmetrical sequence of the columns in the second substrate direction, which in turn advantageously leads to a deformation that is as even as possible during a bending of the silicon substrate about the first substrate direction.

In a further expedient variant embodiment of the method, a square basic surface is employed for the injection structures with a diameter or an edge length less than or equal to 2.5 micrometers, in particular of less than or equal to 2 micrometers.

In a preferred variant embodiment of the method, values of between 2-20 micrometers, in particular up to about 12 micrometers, are employed for the first distance. Preferably this first distance corresponds in this case to a required grating constant in a state in which the microstructure component is used according to specifications as a phase contrast grating.

In a further preferred variant embodiment of the method, values of between 40 and 1300 micrometers, in particular between 40 and 500 micrometers, especially preferably of between 50 and 300 micrometers, are employed for the longitudinal extent of the groups. In particular with longitudinal extents below 1000 micrometers a sufficiently high mechanical stability of the microstructure component is advantageously made possible.

In a further expedient variant embodiment of the method, the drilled holes are formed ("driven forwards") up to a depth of around 400 to 500 micrometers, for example 450 or 470 micrometers. In particular in conjunction with the dimensions of the injection structures described above, this produces an especially high aspect ratio of the drilled holes and thus also of the columns formed therefrom. Preferably in this case the so-called PAECE ("photo assisted electrochemical etching") method is used for this in the first etching step. Preferably, to support this method of etching, a corresponding doping is selected for the silicon substrate. After the etching, the drilled holes in particular have a circular cylindrical structure, i.e. a circular base surface.

In a preferred variant embodiment of the method, for the anisotropically effective etching medium used in the third etching step, a solution is selected that contains potassium hydroxide (KOH), hydrogen peroxide and isopropanol. The result achieved in particular by this is that the drilled holes change from their circular basic surface to a square basic surface and thus grow into square "cylinder holes". In particular, with exact alignment of the first and second substrate direction to the course of the (111) crystal planes of the silicon substrate, the edges of the widened-out drilled holes likewise run exactly along the first and second substrate direction, so that the columns formed have straight edges in these two substrate directions.

In a further expedient variant embodiment of the method, the injection structures are inserted into the first surface in particular through etching by way of a masking layer applied to the first surface, for example a photolithographic layer and/or a ceramic protective layer. The injection structures are transferred in this case in particular after a local opening of the masking layer in the form of circular "holes" or square "holes" matched to the target contour of the injection structures by way of an alkaline, in particular a solution containing potassium hydroxide, into the first surface of the silicon substrate. In particular the injection structures are embodied in this case in the silicon substrate, seen in the depth direction, with a pyramidal structure with a square base surface. The masking layer is preferably removed again after the application of the injection structures.

In particular for the case where the microstructure component involves the phase contrast grating, the grating, after the third etching step—i.e. after the widening-out of the drilled holes to form the respective column—is bent about an axis lying along the first substrate direction (i.e. about the bending axis described above). The bending radius is preferably selected in this case such that the depth direction of each of the columns (or the height direction of the longitudinal webs lying between these columns) is aligned parallel to a local radiation direction occurring when the phase contrast grating is used as per specifications of one of the x-ray beams passing through the phase contrast grating. The bending radius can amount to less than one centimeter in this case.

Preferably the columns in particular, after the bending described above, are filled with a material absorbing x-ray radiation, in particular a metal alloy. For example tin or a tin alloy, tantalum, tungsten, gold or the like are used in such cases. The filling is performed by a casting process, by galvanic or electroless deposition processes for example.

In an expedient variant embodiment of the method, in an additional (fourth) etching step in the rear side (i.e. the second surface) of the silicon substrate, a central area of the silicon substrate, seen in particular in the second substrate direction, is removed (preferably over the complete surface extending in the first substrate direction) and side areas of the second surface, which are arranged, seen in the second substrate direction, at the terminations of the silicon substrate, are left at least in part. In other words these side areas involve edge areas of the silicon substrate, which in this etching step are not removed or are only slightly removed by comparison with the central area. Preferably the side areas are appropriately masked in such cases, so that the etching media used here cannot "attack" these side areas. By the central removal of material the flexural strength of the silicon substrate is further reduced. The edge areas moreover produce a "thickening" of the silicon substrate, which is known to have an increased mechanical stability and can serve as a handling structure. In particular when the microstructure component is used as a phase contrast grating, in the central area (which preferably corresponds to an irradiated area) an absorption of the x-rays in the silicon is also reduced. Preferably this fourth etching step takes place after a filling of the column with the material that absorbs x-rays, so that this material protrudes, in the central area, at least in part in the form of lamellae projecting freely from the remaining silicon substrate.

The inventive microstructure component of at least one embodiment, in particular the phase contrast grating formed by this component, is produced in accordance with the method of at least one embodiment described. Preferably the microstructure component is also bent in the case of the phase contrast grating. In particular, at least one embodiment the inventive microstructure component has the same features and advantages as those produced by the method of production of at least one embodiment described.

In a version advantageous in respect of mechanical stability, the microstructure component has a plurality of columns extending in the first substrate direction (continuous in the thickness direction). Seen in the second substrate direction, these columns are arranged, in respect of their longitudinal extent to one another, offset from column row to column row.

Preferably these columns are filled with the material that absorbs x-rays.

The inventive x-ray device of at least one embodiment, has the phase contrast grating formed by the microstructure component described above. Thus, the inventive x-ray device of at least one embodiment also shares the features and advantages described above. In particular, when the x-ray device is used as per specifications, the columns of the microstructure component described above are filled with the material that absorbs x-rays to form the grating lamellae.

Figure 1:
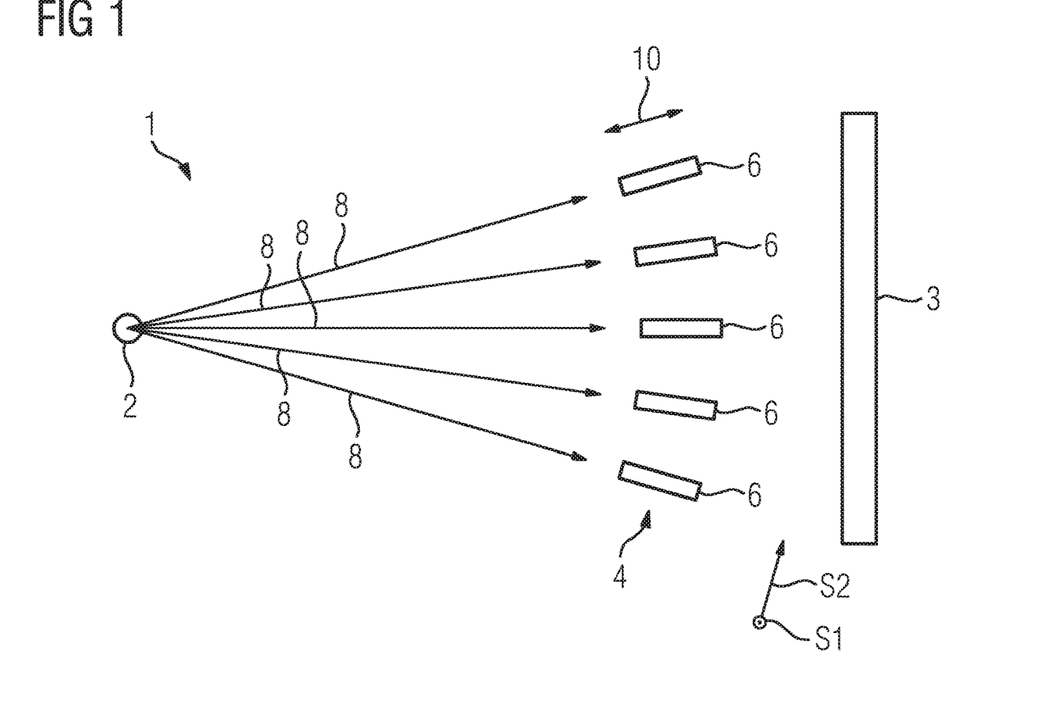
FIG. 1 shows an x-ray device with a phase contrast grating, in a schematic side view.
Figure 2:
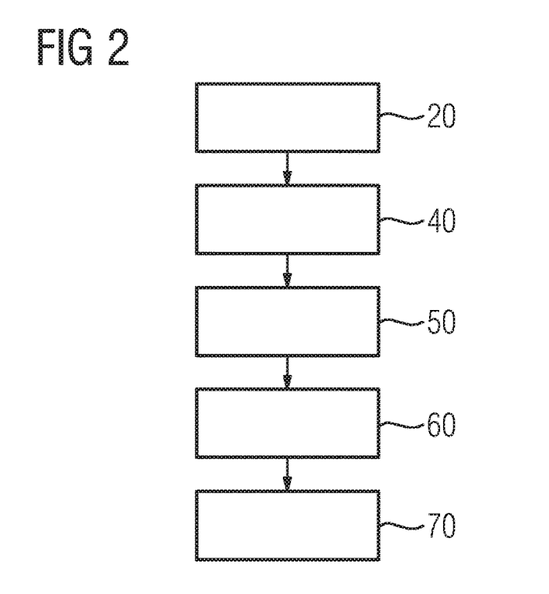
FIG. 2 shows a method for producing the phase contrast grating, in a schematic flow diagram, FIGS. 3, 4 each show, in a schematic view from above, an example embodiment of a grid of injection structures for creating the phase contrast grating from a silicon substrate.

Shown indicated schematically in FIG. 1 is an x-ray device 1. The x-ray device 1 has an x-ray source 2 and an x-ray detector 3. Arranged in the beam path between the x-ray source 2 and the x-ray detector 3 is an (x-ray) phase contrast grating 4. The phase contrast grating 4 in this figure has number of lamellae 6, which are aligned in parallel to the respective local x-ray part beam 8. The phase contrast grating 4 in this case, seen in the thickness direction 10 (or also: in the radiation direction) has dimensions of a maximum of one millimeter. Thus the phase contrast grating 4 involves a component with structures in the micrometer range ("microstructure component"). In order to still be able to mold out the lamellae 6 of the phase contrast grating 4 precisely with such small dimensions, a production method described in greater detail below with reference to FIG. 2 is carried out.

In a first method step 20 in this, method injection structures 22 (cf. FIG. 4) are put into a first surface 24 (see FIG. 5) of a wafer-like silicon substrate 26. In concrete terms the silicon substrate 26 involves a silicon wafer. The injection structures 22 in this case are distributed in a grid 28 over the first surface 24 of the silicon substrate 26. The grid 28 in this case is predetermined (in concrete terms in rows) in a first substrate direction S1 and a second substrate direction S2. I.e. the injection structures 22 are arranged in so-called "column rows" 30, which run in the first substrate direction S1 and repeat in the second substrate direction S2. In the row direction—i.e. in the first substrate direction S1—a number of injection structures 22 in each case (in the present example embodiment in concrete terms seven injection structures 22) are each combined into a group 32. The respective column rows 30, in concrete terms the injection structures 22 arranged next to one another in the second substrate direction S2, are arranged in this case at a first distance A1 from one another. The first distance A1 amounts in the present example embodiment to 12 micrometers and in concrete terms corresponds in this case to a grating constant of the phase constant grating 4. Within the groups 32 the injection structures 22 are arranged at a second distance A2 from one another, which is smaller by a factor of 0.5 than the first distance A1.

Figure 3:
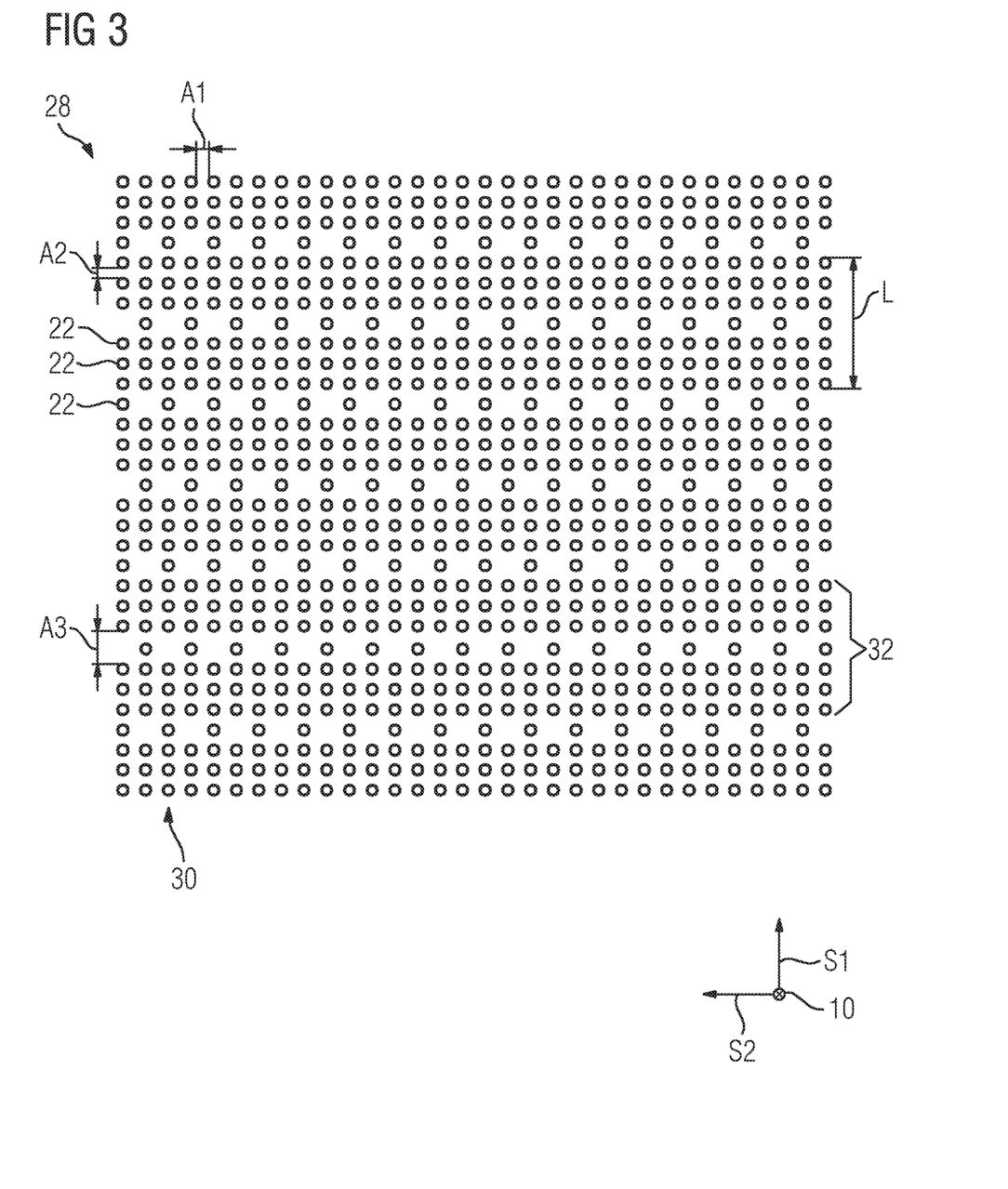
Figure 4:
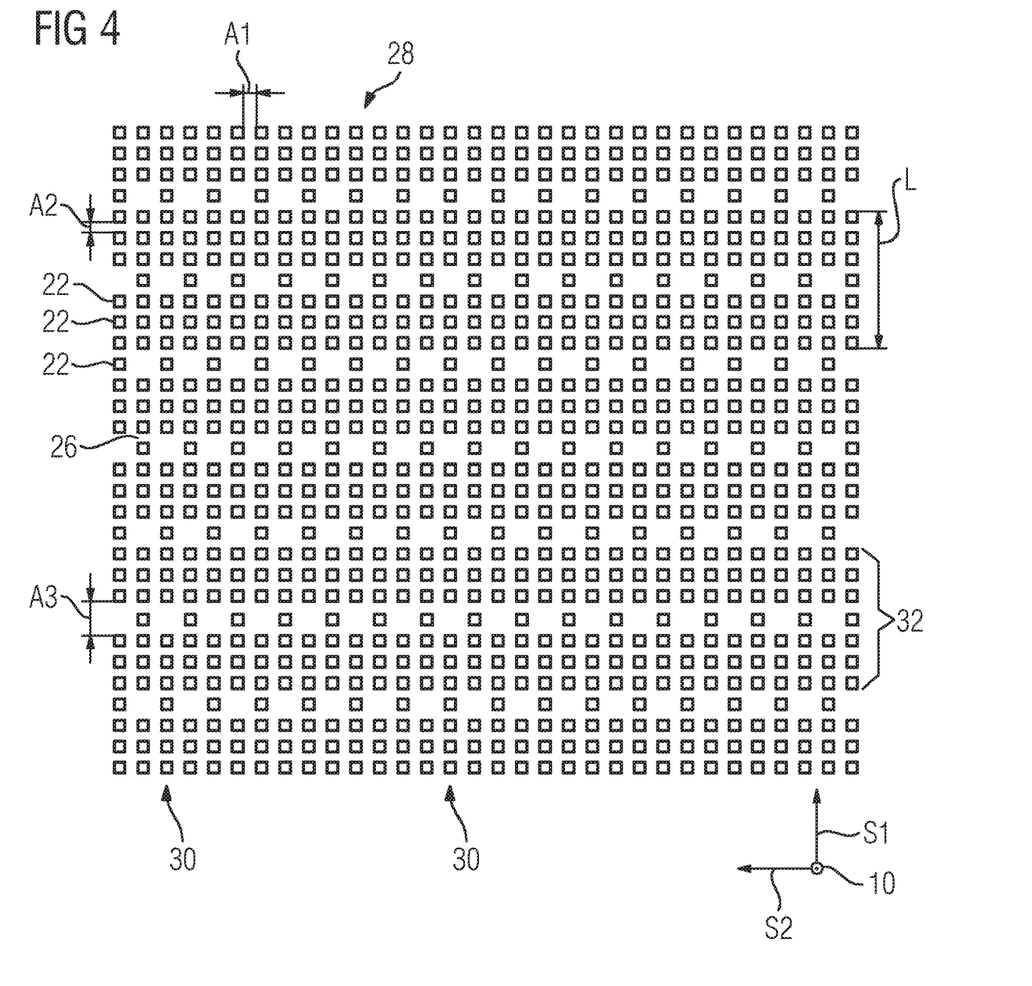

To this end the injection structures 22 are initially embodied as holes in a masking layer (not shown in any greater detail), for example as shown in FIG. 3 in a circular shape or already with the square base area shown in FIG. 4. Subsequently the injection structures are transferred by etching to the first surface 24 of the silicon substrate 26. There they are always molded out with a square basic surface (even in the case of circular-shaped masking). The injection structures 22 are embodied square in this case with an edge length of less than or equal to 2 micrometers. A longitudinal extent LG of the groups 32 thus amounts to around 50 micrometers.

The groups 32 are also arranged at a third distance A3 from one another. The third distance A3 approximately corresponds in this case to leaving out one of the injection structures 22 in the respective column row 30.

In a second method step 40, in an etching step the injection structures 22 are expanded in the thickness direction 10 to form circular drilled holes, of which the side walls are perpendicular to the first surface 24. The so-called PAECE method is used for this. In concrete terms the injection structures 22 are expanded into drilled holes with a depth of 470 micrometers.

In a third method step 50, in a further etching step the second surface 52 lying opposite the first surface 24 is subsequently removed such that the drilled holes are opened on the rear side (i.e. towards the second surface 52). Etching methods such as for example wet-chemical etching with potassium hydroxide or plasma-induced dry etching are used to do this.

Figure 5:
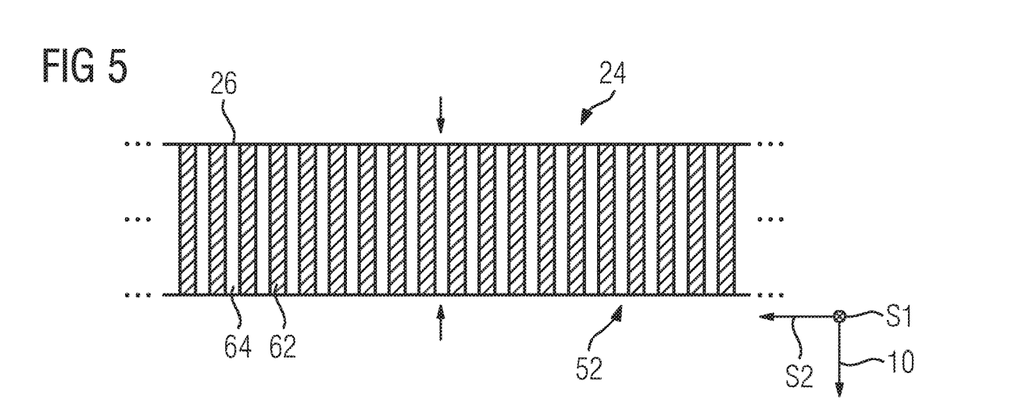
FIG. 5 shows, in a schematic cross-section, an etching step through the silicon substrate.
Figure 6:
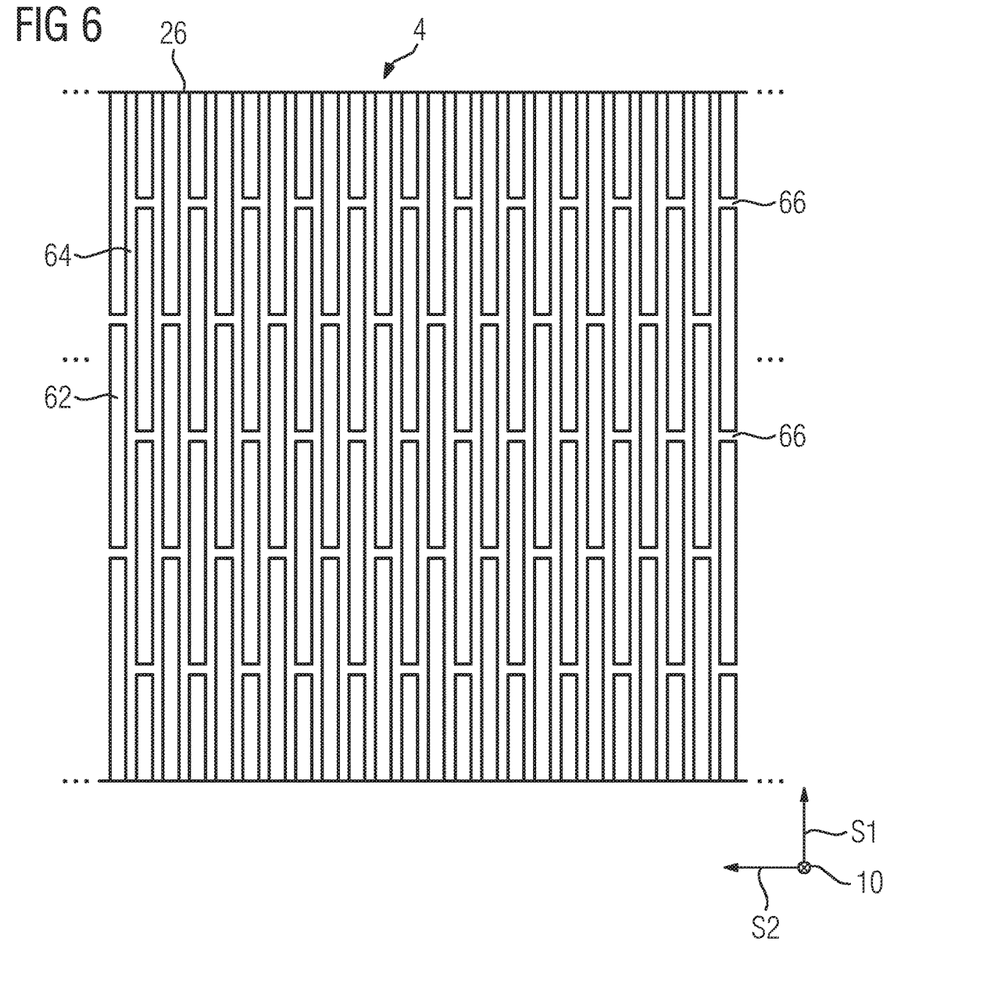
FIG. 6 shows, in a view as depicted in FIG. 3, columns formed from the grid in the silicon substrate.

In a fourth method step 60, in a new etching step the drilled holes are alternately flushed from the first surface 24 and the second surface 52 with an etching medium effective anisotropically (cf. opposing arrows in FIG. 5). The etching medium in this case contains potassium hydroxide, hydrogen peroxide and isopropanol. The first and the second substrate direction S1 or S2 are selected parallel to directions in which (111) crystal planes of the silicon pass through the (100) crystal plane (lying in parallel to the first surface 24). Through this the individual drilled holes are widened out in the first and second substrate direction S1 and S2, so that they have a square cross-section, and unite on continuing widening-out with the adjacent drilled holes within the respective groups 32 to form a column 62 in each case (see FIG. 5, 6). Since the first distance A1 is greater than the second distance A2, longitudinal webs 64 made of silicon remain after the column formation between the individual column rows 30. Because of the third distance A3 between the individual groups 32 a transverse web 66 also remains in each case, seen in the first substrate direction S1, between the columns 62 formed by the groups 32.

The grid 28 is selected in this case such that the groups 32 of two directly adjacent column rows 30 are offset by half of their longitudinal extent L in the first substrate direction S1. This means that the transverse webs 66 of two directly adjacent column rows 30 are not aligned flush with one another. Instead the transverse webs 66 of the "next but one" column rows 30 are always aligned flush with one another. This produces a good compromise between mechanical stability against bending about a bending axis aligned in the first substrate direction S1 and a sufficient flexibility for such bending.

In a further method step 70 the silicon substrate 26 is bent about a bending axis lying in the first substrate direction S1. Subsequently the columns 62 are filled with a metallic material, in concrete terms a tin alloy. The filled columns 62 in this case produce the lamellae 6 shown in FIG. 1.

Figure 7:
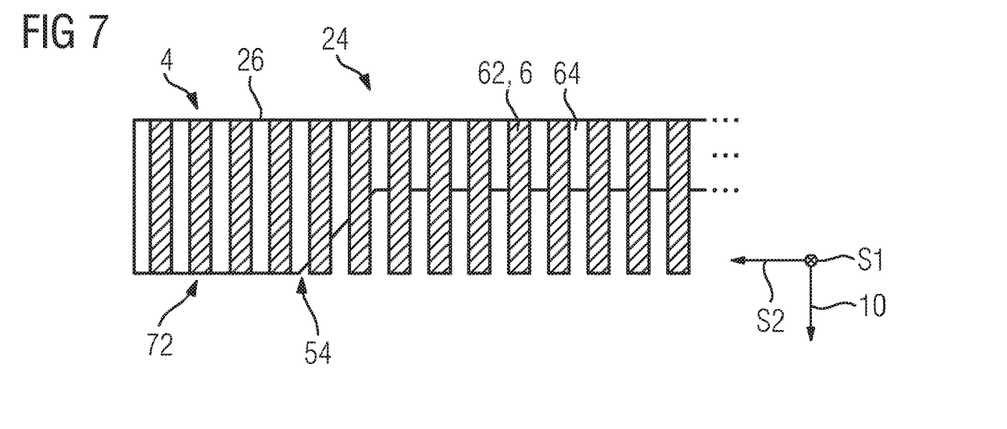
FIG. 7 shows, in a view as depicted in FIG. 5, an optional example embodiment of the phase contrast grating.

In an example embodiment shown in FIG. 7, in a further etching step (in an additional, optional method step) central areas of the rear side (i.e. on the side of the second surface 52) of the silicon substrate 26 in the thickness direction 10 are partly removed. Only in the second substrate direction S2 do terminal edge areas 72 (also: side areas) remain, so that in these edge areas 72 a more massive and thus more mechanically stable handling structure ("grip structure") is present. In concrete terms the edge areas 72 are masked accordingly before the etching. The etching is done by way of potassium hydroxide. The lamellae 6 formed by the tin alloy in the filled columns 62 are at least partly free after this step. The bending of the silicon substrate 26 is not shown in FIG. 7.

The subject matter of the invention is not restricted to the example embodiments described above. Instead, further forms of embodiment of the invention can be derived by the person skilled in the art from the above description. In particular the individual features of the invention and their embodiment variants described on the basis of the different example embodiments can also be combined with one another in another way.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for producing a microstructure component, comprising:
   inserting a plurality of punctiform injection structures in a grid in a first substrate direction and inserting a second substrate direction, standing at right angles to the first substrate direction, into a first surface of a wafer-like silicon substrate;
   lengthening, in a first etching step, the punctiform injection structures into drilled holes in a depth direction of the silicon substrate;
   at least partly removing, in a second etching step, a second surface of the silicon substrate, lying opposite the first surface, for rear-side opening of the drilled holes; and
   pouring in a third etching step, an etching medium, effective anisotropically, alternately through the drilled holes from both surfaces of the silicon substrate, so that drilled holes arranged next to one another in the first substrate direction connect to form a column running in the first substrate direction.

2. The method of claim 1, wherein the punctiform injection structures in the second substrate direction are arranged at a first distance in relation to one another, wherein the punctiform injection structures are combined into groups in the first substrate direction, each of the punctiform injection structures including a subordinate number of the punctiform injection structures, and wherein the punctiform injection structures are arranged within the groups at a second distance reduced by a factor of 0.2 to 0.6, compared to the first distance.

3. The method of claim 2, wherein the groups in the first substrate direction are arranged following one another at a third distance, enlarged in relation to the second distance.

4. The method of claim 3, wherein the groups, which follow each other in the second substrate direction, are arranged in relation to their longitudinal extent offset to one another in the first substrate direction.

5. The method of claim 4, wherein the groups are arranged offset in relation to one another by half of their longitudinal extent.

6. The method of claim 2, wherein the groups, which follow each other in the second substrate direction, are arranged in relation to their longitudinal extent offset to one another in the first substrate direction.

7. The method of claim 6, wherein the groups are arranged offset in relation to one another by half of their longitudinal extent.

8. The method of claim 2, wherein at least one of
a square basic surface with an edge length of less than or equal to 2.5 μm is employed for the punctiform injection structures,
the first distance amounts to 2 to 20 μm, and
the longitudinal extent of the groups amounts to between 40 and 1300 μm.

9. The method of claim 2, wherein the punctiform injection structures are arranged within the groups at a second distance reduced by a factor of 0.3 to 0.5, compared to the first distance.

10. The method of claim 9, wherein the groups in the first substrate direction are arranged following one another at a third distance, enlarged in relation to the second distance.

11. The method of claim 2, wherein the punctiform injection structures are embodied by way of etching a masking layer applied to the first surface, the masking layer having circular or square holes.

12. The method of claim 2, wherein the microstructure component is bent about an axis lying along the first substrate direction after the third etching step.

13. The method of claim 1, wherein the drilled holes are formed out to a depth of around 500 μm.

14. The method of claim 1, wherein a solution containing potassium hydroxide is selected as the anisotropic etching medium used in the third etching step.

15. The method of claim 1, wherein the punctiform injection structures are embodied by way of etching a masking layer applied to the first surface, the masking layer having circular or square holes.

16. The method of claim 1, wherein the microstructure component is bent about an axis lying along the first substrate direction after the third etching step.

17. The method of claim 1, wherein at least one of
the columns are filled with a material that absorbs x-rays, and
in a further etching step, a central area of a rear side of the silicon substrate, seen in the second substrate direction, is removed.

18. A microstructure component, produced according to the method of claim 1.

19. The microstructure component of claim 18, further comprising
a plurality of continuous columns extending longitudinally in the first substrate direction, wherein the columns arranged next to one another in the second substrate direction are offset in relation to one another in respect of their longitudinal extent.

20. An x-ray device comprising:
an x-ray phase contrast grating, formed by the microstructure component of claim 19.

21. An x-ray device comprising:
an x-ray phase contrast grating, formed by the microstructure component of claim 18.

22. An x-ray phase contrast grating, produced according to the method of claim 1.

* * * * *